United States Patent [19]
Cramp et al.

[11] Patent Number: 5,371,063
[45] Date of Patent: Dec. 6, 1994

[54] HERBICIDAL 4-BENZOYLISOXAZOLES

[75] Inventors: Susan M. Cramp; Tibor Musil; Simon N. Pettit; Philip H. G. Smith, all of Essex, England

[73] Assignee: Rhone-Poulenc Agriculture Limited, Essex, England

[21] Appl. No.: 191,449

[22] Filed: Feb. 3, 1994

[30] Foreign Application Priority Data
  Feb. 3, 1993 [GB] United Kingdom ............... 93 02072

[51] Int. Cl.$^5$ ................... A01N 43/74; C07D 261/08
[52] U.S. Cl. ..................................... 504/270; 548/248
[58] Field of Search ......................... 548/248; 504/270

[56] References Cited
  FOREIGN PATENT DOCUMENTS
  0418175  3/1991  European Pat. Off. ............ 548/248
  0487357  5/1992  European Pat. Off. ............ 548/248
  0527036  2/1993  European Pat. Off. ............ 548/248
  0527037  2/1993  European Pat. Off. ............ 548/248

OTHER PUBLICATIONS

CA 115: 8782v Preparation of... Herbicides. Roberts et al., p. 860, 1991.
CA 117: 131182t Preparation of... Herbicides. Cain et al., p. 745, 1992.
CA 118: 234047c Preparation of... Herbicides. Cain et al., p. 1002, 1993.

Primary Examiner—Patricia L. Morris
Assistant Examiner—Joseph K. McKane
Attorney, Agent, or Firm—Burns, Doane, Swecker & Mathis

[57] ABSTRACT

The invention relates to 4-benzoylisoxazole derivatives of formula (I):

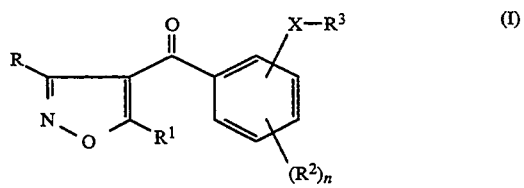

wherein R represents hydrogen or $-CO_2R^4$;
  $R^1$ represents alkyl, haloalkyl or optionally substituted cycloalkyl;
  $R^2$ represents halogen, alkyl, haloalkyl, alkyl substituted by one or more groups $-OR^5$; or a group selected from nitro, cyano, $-CO_2R^5$, $-S(O)_pR^6$, $-O(CH_2)_mOR^5$, $-COR^5$, $-OR^5$ and $-N(R^8)SO_2R^7$;
  $R^3$ represents $-SO_2R^7$;
  X represents the oxygen atom;
  n represents zero or an integer from one to four;
  $R^4$ represents alkyl or haloalkyl;
  $R^5$ and $R^6$, independently represent alkyl, haloalkyl or optionally substituted phenyl;
  $R^7$ represents alkyl, haloalkyl, optionally substituted phenyl or $-NR^5R^6$;
  $R^8$ represents hydrogen, optionally halogenated alkyl, alkenyl or alkynyl; cycloalkyl, optionally substituted phenyl, $-SO_2R^6$ or $-OR^5$;
  p represents zero, one or two; and
  m represents an integer from one to three;
and their use as herbicides is described.

28 Claims, No Drawings

HERBICIDAL 4-BENZOYLISOXAZOLES

This invention relates to novel 4-benzoylisoxazole derivatives, compositions containing them, processes for their preparation and their use as herbicides.

Herbicidal 4-benzoylisoxazoles are described in European Patent Publication Number 0418175.

The present invention provides 4-benzoylisoxazole derivatives of formula (I):

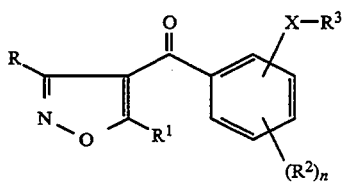

wherein:

R represents the hydrogen atom or a group —$CO_2R^4$;

$R^1$ represents:
a straight- or branched-chain alkyl group containing up to six carbon atoms which is optionally substituted by one or more halogen atoms; or
a cycloalkyl group containing from 3 to 6 carbon atoms optionally substituted by one or more groups $R^5$ or one or more halogen atoms;

$R^2$ represents:
a halogen atom;
a straight- or branched-chain alkyl group containing up to 6 carbon atoms which is optionally substituted by one or more halogen atoms;
a straight- or branched-chain alkyl group containing up to 6 carbon atoms which is substituted by one or more groups —$OR^5$; or
a group selected from nitro, cyano, —$CO_2R^5$, —S(O)$_o$$R^6$, —O(CH$_2$)$_m$$OR^5$, —$COR^5$, —$OR^5$ and —N($R^8$)$SO_2R^7$;

$R^3$ represents —$SO_2R^7$;

X represents the oxygen atom;

n represents zero or an integer from one to four; when n is greater than one the groups $R^2$ may be the same or different;

$R^4$ represents a straight- or branched-chain alkyl group containing up to six carbon atoms which is optionally substituted by one or more halogen atoms;

$R^5$ and $R^6$, which may be the same or different, each represents:
a straight- or branched-chain alkyl group containing up to 6 carbon atoms which is optionally substituted by one or more halogen atoms;
phenyl optionally substituted by from one to five groups $R^2$ which may be the same or different;

$R^7$ represents:
a straight- or branched-chain alkyl group containing up to 6 carbon atoms which is optionally substituted by one or more halogen atoms;
phenyl optionally substituted by from one to five groups $R^2$ which may be the same or different; or
a group —$NR^5R^6$;

$R^8$ represents:
the hydrogen atom;
a straight- or branched-chain alkyl, alkenyl or alkynyl group containing up to six carbon atoms optionally substituted by one or more halogen atoms;
a cycloalkyl group containing from three to six carbon atoms;
phenyl optionally substituted by from one to five groups which may be the same or different selected from halogen, nitro, cyano, $R^5$, S(O)$_{op}R^5$ and —$OR^5$; or
a group selected from —$SO_2R^6$ and —$OR^5$;

p represents zero, one or two;

m represents an integer from one to three; which possess valuable herbicidal properties.

Furthermore in certain cases the groups R, $R^1$, $R^2$, $R^3$, $R^4$, $R^5$, $R^6$, $R^7$ and $R^8$ may give rise to optical isomers. All such forms are embraced by the present invention.

It will be understood that in the above definition $R^2$ does not include substituents containing two or more phenyl rings linked through a bridging group.

The compounds of the invention, in some aspects of their activity, for example in their control of important weeds found in crops, for example *Galium aparine, Amaranthus retroflexus, Setaria faberii* and *Xanthium strumarium*, show advantages over known compounds.

A preferred class of compounds of formula (I) are those in which $R^8$ represents:
the hydrogen atom;
a straight- or branched-chain alkyl, alkenyl or alkynyl group containing up to six carbon atoms which is optionally substituted by one or more halogen atoms; or
a group —$SO_2R^6$.

A further preferred class of compounds of formula (I) are those wherein:

$R^1$ represents a straight- or branched-chain alkyl group containing up to three carbon atoms; cyclopropyl or 1-methylcyclopropyl;

$R^2$ represents:
a halogen atom;
a straight- or branched-chain alkyl group containing up to four carbon atoms which is optionally substituted by one or more halogen atoms;
a straight- or branched-chain alkyl group containing up to four carbon atoms which is substituted by one or more groups —$OR^5$; or
a group selected from nitro, cyano, —$CO_2R^5$, —S(O)$_p$$R^6$, —O(CH$_2$)$_m$$OR^5$, —$OR^5$ and —N($R^8$)$SO_2R^7$;

$R^4$ represents a straight- or branched-chain alkyl group containing up to six carbon atoms;

$R^5$ and $R^6$, which may be the same or different, each represents a straight- or branched-chain alkyl group containing up to four carbon atoms optionally substituted by one or more halogen atoms;

$R^7$ represents a straight- or branched-chain alkyl group containing up to four carbon atoms optionally substituted by one or more halogen atoms;

$R^8$ represents a straight- or branched-chain alkyl group containing up to three carbon atoms;

n represents zero, one or two; and m represents two or three.

A further preferred class of compounds of formula (I) are those wherein:

$R^1$ represents a straight- or branched-chain alkyl group containing up to three carbon atoms; cyclopropyl or 1-methylcyclopropyl;

$R^2$ represents:
a halogen atom;

a straight- or branched-chain alkyl group containing up to four carbon atoms which is optionally substituted by one or more halogen atoms;

a straight- or branched-chain alkyl group containing up to four carbon atoms which is substituted by one or more groups —$OR^5$; or a group selected from —$S(O)_pR^6$, —$O(CH_2)_mOR^5$ and —$OR^5$;

$R^4$ represents a straight- or branched-chain alkyl group containing up to six carbon atoms;

$R^5$ represents an alkyl group containing one or two carbon atoms optionally substituted by one or more halogen atoms;

$R^6$ represents a methyl or ethyl group;

$R^7$ represents a straight- or branched-chain alkyl group containing up to four carbon atoms;

$R^8$ represents a straight- or branched-chain alkyl group containing up to three carbon atoms;

n represents zero, one or two; and m represents two or three.

A further preferred class of compounds of formula (I) are those wherein $R^2$ represents:

a halogen atom;

an alkyl group containing one or two carbon atoms which is optionally substituted by one or more halogen atoms;

—$S(O)_pR^6$ or —$OR^5$;

$R^4$ represents a methyl or ethyl group;

$R^5$ represents an alkyl group containing one or two carbon atoms optionally substituted by one or more halogen atoms;

$R^6$ represents a methyl or ethyl group;

$R^7$ represents a methyl or ethyl group;

$R^8$ represents a straight- or branched-chain alkyl group containing up to three carbon atoms;

n represents zero, one or two; and m represents two.

A further preferred class of compounds of formula (I) are those wherein:

R represents the hydrogen atom;

$R^1$ represents ethyl or cyclopropyl;

$R^2$ represents halogen;

$R^3$ represents —$SO_2R^7$;

X represents the oxygen atom;

n represents zero or one; and $R^7$ represents methyl, ethyl or —$NMe_2$.

Particularly important compounds of formula (I) include the following:

1. 4-[2-Chloro-4-(methylsulphonyloxy)benzoyl]-5-cyclopropylisoxazole.
2. 5-Cyclopropyl-4-[2-(methylsulphonyloxy)benzoyl]isoxazole.
3. 4-[4-Chloro-2-(methylsulphonyloxy)benzoyl]-5-cyclopropylisoxazole.
4. 5-Cyclopropyl-4-[2-(ethylsulphonyloxy)benzoyl]isoxazole.
5. 5-Cyclopropyl-4-[2-(N,N-dimethylaminosulphonyloxy)-benzoyl]isoxazole.
6. 5-Ethyl-4-[2-(methylsulphonyloxy)benzoyl]isoxazole.
7. 4-[5-Chloro-2-(methylsulphonyloxy)benzoyl]-5-cyclopropylisoxazole.

The numbers 1 to 7 are assigned to these compounds for reference and identification hereafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen may be prepared by the reaction of a compound of formula (II):

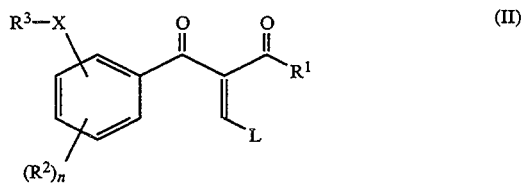

wherein L is a leaving group and $R^1$, $R^2$, $R^3$, n and X are as hereinbefore defined, with hydroxylamine or a salt of hydroxylamine. Hydroxylamine hydrochloride is generally preferred. Generally L is alkoxy, for example ethoxy, or N,N-dialkylamino, for example dimethylamino. The reaction is generally carried out in an organic solvent such as ethanol or acetonitrile or a mixture of a water-miscible organic solvent and water, preferably in a ratio of organic solvent: water of from 1:99 to 99:1, optionally in the presence of a base or acid acceptor such as triethylamine or sodium acetate at a temperature from 0° to 100° C.

According to a further feature of the present invention compounds of formula (I) in which R represents hydrogen may be prepared by the reaction of a compound of formula (III):

wherein $R^1$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —$CO_2R^4$ and $R^2$ represents a group $R^{21}$ which is as hereinbefore defined for $R^2$ provided that p is 0 or 2, may be prepared by the reaction of a compound of formula (IV)

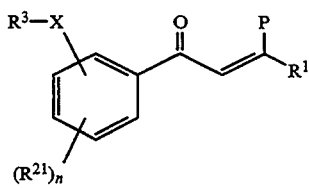

wherein R¹, R²¹, R³, X and n are as hereinbefore defined and P is a leaving group such as N,N-dialkylamino, with a compound of formula R⁴O₂CC(Z)=NOH wherein R⁴ is as hereinbefore defined and Z is a halogen atom. Generally Z is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group —CO₂R⁴ and R² represents a group R²¹ as hereinbefore defined, may be prepared by the reaction of a compound of formula (V):

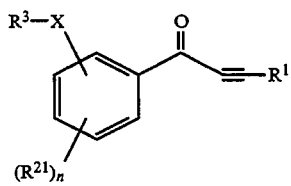

wherein R¹, R²¹, R³, X and n are as hereinbefore defined, with a compound of formula R⁴O₂CC(Z)=NOH wherein Z and R⁴ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents —CO₂R⁴ and R² represents a group R²¹ as hereinbefore defined, may be prepared by the reaction of a salt of a compound of formula (VI):

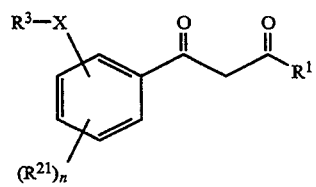

wherein R¹, R²¹, R³, X and n are as hereinbefore defined, with a compound of formula R⁴O₂CC(Z)=NOH wherein R⁴ and Z are as hereinbefore defined. Preferred salts include sodium or magnesium salts. The reaction may be performed in an inert solvent such as dichloromethane or acetonitrile at a temperature between room temperature and the reflux temperature of the mixture.

Intermediates in the preparation of compounds of formula (I) may be prepared by the application or adaptation of known methods.

Compounds of formula (II) may be prepared by the reaction of compounds of formula (VI) with either a trialkyl orthoformate such as triethyl orthoformate or a dimethylformamide dialkyl acetal such as dimethylformamide dimethyl acetal.

The reaction with triethyl orthoformate can be carried out in the presence of acetic anhydride at the reflux temperature of the mixture and the reaction with dimethylformamide dialkyl acetal is carried out optionally in the presence of an inert solvent at a temperature from room temperature to the reflux temperature of the mixture.

Compounds of formula (IV) may be prepared by the reaction of a compound of formula (VII) with a benzoyl chloride of formula (VIII):

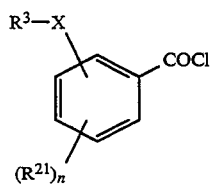

wherein R¹, R²¹, R³, X, n and P are as hereinbefore defined.

The reaction is generally carried out in the presence of an organic base such as triethylamine in an inert solvent such as toluene or dichloromethane at a temperature between −20° C. and room temperature.

Compounds of formula (V) may be prepared by the metallation of the appropriate acetylene of formula (IX):

followed by reaction of the metal salt thus obtained with a benzoyl chloride of formula (VIII). The metallation is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Compounds of formula (VI) may be prepared by the reaction of an acid chloride of formula (VIII) with the metal salt of a compound of formula (X):

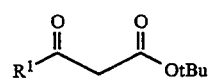

wherein R¹ is as hereinbefore defined, to give a compound of formula (XI):

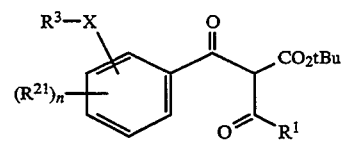

wherein R¹, R²¹, R³, X and n are as hereinbefore defined, which is subsequently decarboxylated to give a compound of formula (VI). The reaction to produce the metal salt of a compound of formula (X) is generally performed in a solvent such as a lower alcohol, preferably methanol. Preferably the metal is magnesium. The metal salt of the compound of formula (X) is subsequently reacted with an acid chloride of formula (VIII) in an inert solvent such as toluene or acetonitrile. The decarboxylation is generally performed by refluxing the compound of formula (XI) in the presence of a catalyst, such as paratoluenesulphonic acid, in an inert solvent e.g. toluene.

Acid chlorides of formula (VIII) may be prepared by the reaction of a benzoic acid of formula (XII):

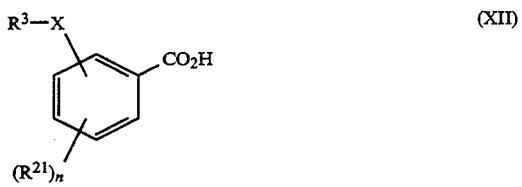

(XII)

wherein $R^{21}$, $R^3$, X and n are as hereinbefore defined, with a chlorinating agent, for example thionyl chloride at the reflux temperature of the mixture.

Intermediates of formulae (III), (VII), (IX), (X) and (XII) are known or may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p is one or two may be prepared by the oxidation of the sulphur atom of the corresponding compounds in which p is zero or one. The oxidation of the sulphur atom is generally carried out using for example 3-chloroperoxybenzoic acid in an inert solvent such as dichloromethane at a temperature from −40° C. to room temperature, or hydrogen peroxide in acetic acid in the presence of acetic anhydride or concentrated sulphuric acid.

The following examples illustrate the preparation of compounds of formula (I) and the following reference examples illustrate the preparation of intermediates of the invention. In the present specification b.p. means boiling point; m.p. means melting point; cPr represents cyclopropyl.

EXAMPLE 1

Sodium acetate (1.52 g) was added to a stirred mixture of 1-[2-chloro-4-(methylsulphonyloxy)phenyl]-3-cyclopropyl-2-ethoxymethylenepropan-1,3-dione (5.6 g) and hydroxylamine hydrochloride (1.3 g) in ethanol. The mixture was stirred for 0.75 hours. Water was added and the mixture was extracted with dichloromethane. The organic layer was washed with water, dried (MgSO$_4$) and filtered. The filtrate was evaporated to dryness and the residue was purified by chromatography eluted with a mixture of ethyl acetate and dichloromethane to give 4-[2-chloro-4-(methylsulphonyloxy)benzoyl]-5-cyclopropylisoxazole (compound 1, 4.60 g) as a brown oil, NMR (CDCl$_3$) 1.25–1.35(m,2H), 1,4–1.5 (m,2H), 2.6–2.7(m, 1H), 3.2(s, 1H), 7.3(d, 1H), 7.4(s, 1H), 7.45 (d, 1H), 8.15 (s, 1H).

By proceeding in a similar manner the following compounds of formula I were prepared from the appropriately substituted starting materials.

| Cpd. No. | R | $R^1$ | $(R^2)_n$ | $XR^3$ | m.p./NMR |
|---|---|---|---|---|---|
| 2 | H | cPr | — | 2-OSO$_2$Me | a |
| 3 | H | cPr | 4-Cl | 2-OSO$_2$Me | 71–73° C. |
| 4 | H | cPr | — | 2-OSO$_2$Et | b |
| 5 | H | cPr | — | 2-OSO$_2$NMe$_2$ | c |
| 6 | H | Et | — | 2-OSO$_2$Me | 57–61° C. |
| 7 | H | cPr | 5-Cl | 2-OSO$_2$Me | 110–113° C. |

Note:
a NMR (CDCl$_3$)1.1–1.2(m, 2H), 1.25–1.35(m, 2H), 2.5–2.6(m, 1H), 3.1(s, 3H), 7.3–7.6(m, 4H), 8,2(s, 1H).
b NMR (CDCl$_3$)1.15–1.3(m, 2H), 1.3–1.4(m, 2H), 1.45(t, 3H), 2.55–2.7(m, 1H), 3.3(q, 2H), 7.35–7.7(m, 4H), 8.25(s, 1H).
c NMR (CDCl$_3$)1.15–1.25(m, 2H), 1.25–1.35(m, 2H), 2.55–2.7(m, 1H), 2.35(s, 6H), 7.35–7.6(m, 4H), 8.25(s, 1H).

REFERENCE EXAMPLE 1

A mixture of 1-[2-chloro-4-(methylsulphonyloxy)phenyl]-3-cyclopropylpropan-1.3-dione (4.75 g) and triethyl orthoformate (4.5 g) in acetic anhydride was stirred and heated at reflux for 3 hours. The mixture was cooled and evaporated to dryness. Toluene was added and the mixture was re-evaporated to give 1-[2-chloro-4-(methylsulphonyloxy)phenyl]-3-cyclopropyl-2-ethoxymethylenepropan-1,3-dione (5.7 g) as a brown oil which was not further purified.

By proceeding in a similar manner the following compounds were prepared from the appropriately substituted starting materials;

| $R^1$ | $(R^2)n$ | $XR^3$ |
|---|---|---|
| cPr | — | 2-OSO$_2$Me |
| cPr | 4-Cl | 2-OSO$_2$Me |
| cPr | — | 2-OSO$_2$Et |
| cPr | — | 2-OSO$_2$NMe$_2$ |
| Et | — | 2-OSO$_2$Me |
| cPr | 5-Cl | 2-OSO$_2$Me |

REFERENCE EXAMPLE 2

A suspension of magnesium (0.47 g) in methanol was stirred and heated at reflux for 0.5 hours. t-Butyl 3-cyclopropyl-3-oxopropionate was added and the mixture was heated at reflux for 0.5 hours. The mixture was cooled and evaporated. Toluene was added and the mixture was re-evaporated. The residue was redissolved in toluene and a solution of 2-chloro-4-(methylsulphonyloxy)benzoyl chloride (5.1 g) in toluene was added. The mixture was stirred at room temperature overnight. Hydrochloric acid (2M) was added and the mixture was stirred for half an hour. The layers were separated and the organic layer was washed with water and dried azeotropically. p-Toluene sulphonic acid (0.5 g) was added and the mixture was heated at reflux for 2.5 hours. It was cooled, washed with water, dried (MgSO$_4$) and filtered. The filtrate was evaporated to dryness to give 1-[2-chloro-4-(methylsulphonyloxy))- phenyl]-3-cyclopropylpropan-1,3-dione (6.05 g) as a brown solid m.p. 74°–77° C.

By proceeding in a similar manner the following compounds of formula (VI) above were prepared from the appropriately substituted starting materials;

| $R^1$ | $(R^2)_n$ | $XR^3$ | m.p./NMR |
|-------|-----------|--------|----------|
| cPr | — | 2-OSO$_2$Me | a |
| cPr | 4-Cl | 2-OSO$_2$Me | b |
| cPr | — | 2-OSO$_2$Et | c |
| cPr | — | 2-OSO$_2$NMe$_2$ | 57–59° C. |
| Et | — | 2-OSO$_2$Me | d |
| cPr | 5-Cl | 2-OSO$_2$Me | e |

Note:
a NMR(CDCl$_3$)0.9–1.05(m, 2H), 1.1–1.2(m, 2H), 1.7–1.8(m, 1H), 3.1(s, 3H), 6.15(s, 1H), 7.25–7.5(m, 3H), 7.65(d, 1H), 15.85–16.3(bs, 1H).
b NMR(CDCl$_3$)0.8–0.9(m, 2H), 1.0–1.15(m, 2H), 1.6–1.7(m, 1H), 3.05(s, 3H), 6.1(s, 1H), 7.25(d, 1H), 7.35(s, 1H), 7.55(d, 1H).
c NMR(CDCl$_3$)0.9–1.1(m, 2H), 1.2–1.3(m, 2H), 1.5(t, 3H), 1.7–1.85(m, 1H), 3.3(q, 2H), 6.2(s, 1H), 7.3–7.55(m, 3H), 7.75(d, 1H), 15.9–16.2(bs, 1H).
d NMR(CDCl$_3$)1.25(t, 3H), 2.45(q, 2H), 3.15(s, 1H), 6.1(s, 1H), 7.3–7.65(m, 3H), 7.75(d, 1H), 15.6–15.95(bs, 1H).
e NMR(CDCl$_3$)0.9–1.15(m, 2H), 1.2–1.3(m, 2H), 1.7–1.85(m, 1H), 3.15(s, 3H), 6.2(s, 1H), 7.3–7.55(m, 2H), 7.75(s, 1H), 15.85–16.25(bs, 1H).

Benzoyl chlorides were prepared by heating the appropriate benzoic acid in thionyl chloride at reflux for 2 hours. After cooling, the excess thionyl chloride was removed by evaporation. Toluene was added and the mixture was re-evaporated to give the crude benzoyl chlorides which were used without further purification.

REFERENCE EXAMPLE 3

A mixture of methyl 2-(methylsulphonyloxy)benzoate (6.9 g) in hydrochloric acid (6M) was heated at reflux for 0.75 hours. The cooled mixture was diluted with ether and extracted with ethyl acetate. The organic layer was washed with aqueous sodium chloride solution. dried (MgSO$_4$) and filtered. The filtrate was evaporated to dryness to give 2-(methylsulphonyloxy)-benzoic acid (6.1 g) as a white solid m.p. 125°–126° C.

By proceeding in a similar manner the following compounds were prepared from the appropriately substituted starting materials.

4-Chloro-2-(methylsulphonyloxy)benzoic, acid m.p. 167°–170° C.

2-(Ethylsulphonyloxy)benzoic acid, m.p. 101.7°–103.2° C.

2-(N,N-Dimethylaminosulphonyloxy)benzoic acid, m.p. 108.5°–111.5° C.

5-Chloro-2-(methylsulphonyloxy)benzoic acid, m.p. 148°–156° C.

REFERENCE EXAMPLE 4

Methane sulphonyl chloride (7.0 g) was added to a stirred, cooled mixture of methyl 4-chlorosalicylate (10.0 g) and triethylamine (8.0 g) in dichloromethane while maintaining the temperature at 0° C. The mixture was then stirred at room temperature for one-half hour and left to stand overnight. The mixture was washed with hydrochloric acid (2M), saturated aqueous sodium bicarbonate solution, water, dried (Na$_2$SO$_4$) and filtered. The filtrate was evaporated to dryness to give methyl 4-chloro-2-(methylsulphonyloxy)benzoate (11.7 g) as an orange solid m.p. 82.5°–84.5° C.

By proceeding in a similar manner the following compounds were prepared from the appropriately substituted starting materials.

Methyl 2-(ethylsulphonyloxy)benzoate NMR (CDCl$_3$) 1.5(t,3H), 3.4(q,2H), 3.85(s,3H), 7.25–7.4(m,2H), 7.5(m, 1H), 7.9(d, 1H).

Methyl 5-chloro-2-(methylsulphonyloxy)benzoate NMR (CDCl$_3$) 3.3(s,3H), 3.95(s,3H), 7.35(d, 1H), 7.55(d, 1H), 7.95(s, 1H).

REFERENCE EXAMPLE 5

Dimethylaminosulphonyl chloride (17.2 g) was added to a mixture of methyl salicylate (15.2 g) and potassium carbonate (27.6 g) in acetonitrile. The mixture was stirred at room temperature for 1 hour. TDA-1 (2.0 g) was added and the mixture stirred at room temperature for 24 hours. The mixture was filtered and the filtrate was evaporated to dryness. The residue was dissolved in dichloromethane, washed with water, dried (MgSO$_4$) and filtered. The filtrate was evaporated to dryness and the residue was triturated with ether. The solid was filtered off and purified by chromatography eluted with dichloromethane to give methyl 2-(dimethylaminosulphonyloxy)benzoate (17.4 g) as a white solid m.p. 75.5°–76.5° C.

According to a feature of the present invention, there is provided a method for controlling the growth of weeds (i.e. undesired vegetation) at a locus which comprises applying to the locus a herbicidally effective amount of at least one isoxazole derivative of formula (I). For this purpose, the isoxazole derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application. By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranthus retroflexus, Bidens pilosa, Chenopodium album, Gallium aparine, Ipomoea spp.* e.g. *Ipomoea purpurea, Sesbania exaltata, Sinapis arvensis, Solanum nigrum* and *Xanthium strumarium*, and grass weeds, for example *Alopecurus myosuroides, Avena fatua, Digitaria sanguinalis, Echinochloa crus-galli, Sorghum bicolor, Eleusine indica* and *Setaria spp*, e.g. *Setaria faberii* or *Setaria viridis*, and sedges, for example, *Cyperus esculentus.*

The amounts of compounds of formula (I) applied vary with the nature of the weeds, the compositions used, the time of application, the climatic and edaphic conditions and (when used to control the growth of weeds in crop-growing areas) the nature of the crops.

When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose. When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the isoxazole derivatives of formula (I), in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or nonionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminum silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, coloring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 40% of sodium carbonate and from 0 to 88% of solid diluent;

liquid water soluble concentrates which comprise from 5 to 50%, e.g. 10 to 30%, of one or more compounds of formula (I), from to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier; and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino- 1,3,5-triazine], bromoxynil[3,5-dibromo-4-hydroxybenzonitrile], chlortoluron [N$\alpha$-(3-chloro-4-methylphenyl)-N,N-dimethylurea], cyanazine [2-chloro-4-(1-cyano-1- methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2- dimethyl-3,5-diphenylpyrazolium salts], flampropmethyl[methyl N-2-(N-benzoyl-3-chloro-4-fluoroanilino)-propionate], fluometuron [N'-(3-trifluoromethylphenyl)-N,N-dimethylurea], isoproturon[N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl- benzimidazol-2-yl)carbamate, and triazoles e.g. 1-(4-chloro-phenoxy)-3,3- dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the isoxazole derivatives of formula (I) or, as is preferred, a herbicidal composition as hereinbefore described, and preferably a herbicidal concentrate which must be diluted before use, comprising at least one of the isoxazole derivatives of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7-8 is obtained then making up to volume with water.

Similar soluble concentrates may be prepared as described above by replacing the isoxazole (compound 1) with other compounds of formula (I).

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal applications according to the following procedures.

METHOD OF USE OF HERBICIDAL COMPOUNDS:

a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20-24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| Weed species | Number of plants per pot | Growth stage |
|---|---|---|
| 1) Broad leafed weeds | | |
| Abutilon theophrasti | 3 | 1-2 leaves |
| Amaranthus retroflexus | 4 | 1-2 leaves |
| Galium aparine | 3 | 1st whorl |
| Ipomoea purpurea | 3 | 1-2 leaves |
| Sinapis arvensis | 4 | 2 leaves |
| Xanthium strumarium | 1 | 2-3 leaves. |
| 2) Grass weeds | | |
| Alopecurus myosuroides | 8-12 | 1-2 leaves |
| Avena fatua | 12-18 | 1-2 leaves |
| Echinochloa crus-galli | 4 | 2-3 leaves |
| Setaria viridis | 15-25 | 1-2 leaves. |
| 3) Sedges | | |
| Cyperus esculentus | 3 | 3 leaves. |

| | Number of plants per pot | Growth stage |
|---|---|---|
| Crops | | |
| 1) Broad leafed | | |
| Cotton | 2 | 1 leaf |
| Soya | 2 | 2 leaves. |
| 2) Grass | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention, used at 4 kg/ha or less, have shown an excellent level of herbicidal activity together with crop tolerance on the weeds used in the foregoing experiments.

When applied pre- or post-emergence at 1000 g/ha compounds 1 to 7 gave at least 90% reduction in growth of one or more of the weed species.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound of the formula:

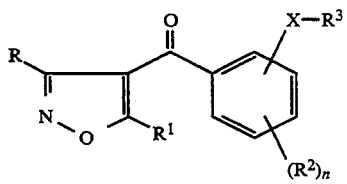

(I)

wherein:

R is hydrogen or —$CO_2R^4$;

$R^1$ is:
straight- or branched-chain alkyl having up to six carbon atoms, optionally substituted by one or more halogen; or
cycloalkyl having from 3 to 6 carbon atoms, optionally substituted by one or more $R^5$ groups or one or more halogen;

$R^2$ is:
halogen;
straight- or branched-chain alkyl having up to 6 carbon atoms, optionally substituted by one or more halogen;
straight- or branched-chain alkyl having up to 6 carbon atoms which is substituted by one or more —$OR^5$ groups; or
a member selected from the group consisting of nitro, cyano, —$CO_2R^5$, —$S(O)_pR^6$, —$O(CH_2)_mOR^5$, —$COR^5$, —$OR^5$ and —$N(R^8)SO_2R^7$;

$R^3$ is —$SO_2R^7$;

X is oxygen;

n is zero or an integer from one to four; when n is greater than one, then the $R^2$ groups can be the same or different;

$R^4$ is straight- or branched chain-alkyl having up to six carbon atoms, optionally substituted by one or more halogen;

each of $R^5$ and $R^6$, which can be the same or different, is:
straight- or branched-chain alkyl having up to 6 carbon atoms, optionally substituted by one or more halogen; or
phenyl, optionally substituted by from one to five $R^2$groups, which can be the same or different;

$R^7$ is:
straight- or branched-chain alkyl having up to 6 carbon atoms, optionally substituted by one or more halogen;
phenyl, optionally substituted by from one to five $R^2$groups, which can be the same or different; or
—$NR^5R^6$;

$R^8$ is:
hydrogen;
straight- or branched-chain alkyl, alkenyl or alkynyl having up to six carbon atoms, optionally substituted by one or more halogen;
cycloalkyl having from three to six carbon atoms;
phenyl, optionally having from one to five substituents, which can be the same or different, selected from the group consisting of halogen nitro, cyano, $R^5$ $S(O)_pR^5$ and —$OR^5$; or
a member selected from the group consisting of —$SO_2R^6$ and —$OR^5$;

p is zero, one or two; and m is an integer from one to three.

2. A compound according to claim 1 wherein:
$R^8$ is:
hydrogen;
straight- or branched-chain alkyl, alkenyl or alkynyl having up to six carbon atoms, optionally substituted by one or more halogen; or
an —$SO_2R^6$group, wherein $R^6$ is as defined in claim 1.

3. A compound according to claim 1 wherein:
$R^1$ is straight- or branched-chain alkyl having up to three carbon atoms, cyclopropyl or 1-methylcyclopropyl;
$R^2$ is:
halogen;
straight- or branched-chain alkyl having up to four carbon atoms, optionally substituted by one or more halogen;
straight- or branched-chain alkyl having up to four carbon atoms which is substituted by one or more —$OR^5$ groups; or
member selected from the group consisting of nitro, cyano, —$CO_2R^5$, —$S(O)_pR^6$, —$O(CH_2)_mOR^5$, —$OR^5$ and —$N(R^8)SO_2R^7$;

$R^4$ is straight- or branched-chain alkyl having up to six carbon atoms;

each of $R^5$ and $R^6$, which can be the same or different, is straight- or branched-chain alkyl having up to four carbon atoms, optionally substituted by one or more halogen;

$R^7$ is straight- or branched-chain alkyl having up to four carbon atoms, optionally substituted by one or more halogen;

$R^8$ is straight- or branched-chain alkyl having up to three carbon atoms;

n is zero, one or two; and m is two or three.

4. A compound according to claim 1 wherein:

$R^1$ is straight- or branched-chain alkyl having up to three carbon atoms, cyclopropyl or 1-methylcyclopropyl;

$R^2$ is:
halogen;
straight- or branched-chain alkyl having up to four carbon atoms, optionally substituted by one or more halogen;
straight- or branched-chain alkyl having up to four carbon atoms which is substituted by one or more —$OR^5$ groups; or
a member selected from the group consisting of —$S(O)_pR^6$, —$O(CH_2)_mOR^5$ and —$OR^5$;

$R^4$ is straight- or branched-chain alkyl having up to six carbon atoms;

$R^5$ is alkyl having one or two carbon atoms, optionally substituted by one or more halogen;

$R^6$ is methyl or ethyl;

$R^7$ is straight- or branched-chain alkyl having up to four carbon atoms;

$R^8$ is straight- or branched-chain alkyl having up to three carbon atoms;

n is zero, one or two; and m is two or three.

5. A compound according to claim 1 wherein:

$R^2$ is:
halogen;
alkyl having one or two carbon atoms, optionally substituted by one or more halogen;
—$S(O)_pR^6$; or
—$OR^5$;

$R^4$ is methyl or ethyl;

$R^5$ is alkyl having one or two carbon atoms, optionally substituted by one or more halogen;

$R^6$ is methyl or ethyl;

$R^7$ is methyl or ethyl;

$R^8$ is straight- or branched-chain alkyl having up to three carbon atoms;

n is zero, one or two; and m is two.

6. A compound according to claim 1 wherein:

R is hydrogen;

$R^1$ is ethyl or cyclopropyl;

$R^2$ is halogen;

$R^3$ is —$SO_2R^7$;

X is oxygen;

n is zero or one; and $R^7$ is methyl, ethyl or dimethylamino.

7. A compound according to claim 1 wherein R is hydrogen.

8. A compound according to claim 1 wherein $R^1$ is straight- or branched-chain alkyl having up to three carbon atoms, cyclopropyl or 1-methylcyclopropyl.

9. A compound according to claim 8 wherein $R^1$ is ethyl or cyclopropyl.

10. A compound according to claim 1 wherein n is zero, one or two.

11. A compound according to claim 10 wherein n is zero or one.

12. A compound according to claim 1 wherein $R^2$ is halogen.

13. A compound according to claim 1 wherein $R^2$ is straight- or branched-chain alkyl having up to four carbon atoms, optionally substituted by one or more halogen.

14. A compound according to claim 1 wherein $R^2$ is straight- or branched-chain alkyl having up to four carbon atoms which is substituted by one or more —$OR^5$ groups.

15. A compound according to claim 1 wherein $R^2$ is a member selected from the group consisting of —$S(O)_pR^6$, —$O(CH_2)_mOR^5$ and —$OR^5$.

16. A compound according to claim 1 wherein X is oxygen and $R^3$ is —$SO_2R^7$ wherein $R^7$ is straight- or branched-chain alkyl having up to four carbon atoms or —$NR^5R^6$.

17. A compound according to claim 16 wherein $R^7$ is methyl, ethyl or dimethylamino.

18. A compound according to claim 1 wherein $R^4$ is straight- or branched-chain alkyl having up to six carbon atoms.

19. A compound according to claim 18 wherein $R^4$ is methyl or ethyl.

20. A compound according to claim 1, wherein $R^5$ is alkyl having one or two carbon atoms, optionally substituted by one or more halogen.

21. A compound according to claim 1 wherein $R^6$ is methyl or ethyl.

22. A compound according to claim 1 wherein $R^8$ is straight- or branched-chain alkyl having up to three carbon atoms.

23. A compound according to claim 1 wherein m is two or three.

24. The compound according to claim 1 which is:
4-[2-chloro-4-(methylsulphonyloxy)benzoyl]-5-cyclopropylisoxazole;
5-cyclopropyl-4-[2-methylsulphonyloxy)benzoyloxy)benzoyl]isoxazole;
4-[4-chloro-2-(methylsulphonyloxy)benzoyl]-5-cyclopropylisoxazole;
5-cyclopropyl-4-[2-(ethylsulphonyloxy)benzoyl]isozazole;
5-cyclopropyl-4-[2-(N,N-dimethylaminosulphonyloxy)-benzoyl]isoxazole;
5-ethyl-4-[2-(methylsulphonyloxy)benzoyl]isoxazole; or
4-[5-chloro-2-(methylsulphonyloxy)benzoyl]-5-cyclopropylisoxazole.

25. A herbicidal composition which comprises:
(a) a herbicidally effective amount of a compound of formula (I) as defined in claim 1; and
(b) at least one member selected from the group consisting of an agriculturally acceptable carrier and an agriculturally acceptable surface active agent.

26. A herbicidal composition according to claim 25 in the form of an aqueous suspension concentrate, a wettable powder, a water soluble or water dispersible powder, a liquid water soluble concentrate, a liquid emulsifiable suspension concentrate, a granule or an emulsifiable concentrate.

27. A method for controlling the growth of weeds at a locus which comprises applying to said locus a herbicidally effective amount of a compound of formula (I) as defined in claim 1.

28. A method according to claim 27 wherein the locus is an area used, or to be used, for the growing of crops and the compound is applied at an application rate of from about 0.01 kg to about 4.0 kg per hectare.

* * * * *